United States Patent [19]

Nees

[11] Patent Number: 4,762,794

[45] Date of Patent: Aug. 9, 1988

[54] APPARATUS FOR CONTACTING BIOLOGICAL CELL SYSTEMS WITH A PERFUSION FLUID

[76] Inventor: Stephan Nees, Waldwiesenstr. 30b, München, Fed. Rep. of Germany

[21] Appl. No.: 609,871

[22] Filed: May 14, 1984

[30] Foreign Application Priority Data

May 13, 1983 [DE] Fed. Rep. of Germany ....... 3317551

[51] Int. Cl.$^4$ .................. C12M 3/00; C12M 3/04; C12M 1/14
[52] U.S. Cl. .................. 435/284; 435/285; 435/310; 435/1; 417/437
[58] Field of Search ............ 435/284, 285, 286, 283, 435/287, 299, 310, 311, 1; 210/416.1, 321.3, 321.75, 321.84; 222/380, 383, 135; 417/437, 521

[56] References Cited

U.S. PATENT DOCUMENTS

| | | | |
|---|---|---|---|
| 2,896,840 | 7/1959 | Hendry | 210/416.1 X |
| 3,027,305 | 3/1962 | Freeman | 435/310 X |
| 3,294,031 | 12/1966 | Latawic | 417/436 |
| 3,378,143 | 4/1968 | Tipping | 210/416.1 X |
| 3,570,672 | 3/1971 | Bach | 210/134 |
| 3,843,455 | 10/1974 | Bier | 435/283 |
| 3,864,248 | 2/1975 | Granger et al. | 210/356 X |
| 3,914,954 | 10/1975 | Doerig | 435/283 X |
| 3,919,053 | 11/1975 | Nazemi | 435/313 |
| 4,086,036 | 4/1978 | Hagen et al. | 417/413 |
| 4,201,845 | 5/1980 | Feder et al. | 435/285 |
| 4,446,234 | 5/1984 | Russo et al. | 435/284 X |

FOREIGN PATENT DOCUMENTS

| | | | |
|---|---|---|---|
| 0200497 | 5/1983 | German Democratic Rep. | 435/283 |
| 1181174 | 2/1970 | United Kingdom | 435/288 |

Primary Examiner—Robert J. Warden
Assistant Examiner—Randall E. Deck
Attorney, Agent, or Firm—Peter K. Kontler

[57] ABSTRACT

Apparatus for contacting a biological cell system on a substrate with a pulsating flow of perfusion fluid has a two-part housing for a combined holding and tensioning device which is removably inserted into an internal space to define with the housing and with the substrate therein two separate chambers. The housing has inlets and outlets for the two chambers and inlet and outlet valves which are operated in response to a reduction or increase of the volume of the respective chambers by elastic walls of the housing. The walls are oscillatable by cams and cam followers and the valves at the inlets open when the valves at the respective outlets are closed and vice versa. The characteristics of perfusion fluid prior to entry into and upon evacuation from the chambers are monitored to thus ascertain the nature of processes which take place at the cells on the substrate.

10 Claims, 4 Drawing Sheets

APPARATUS FOR CONTACTING BIOLOGICAL CELL SYSTEMS WITH A PERFUSION FLUID

The invention relates to perfusion apparatus for contacting with a perfusion fluid biological cell systems supported on a substrate.

For investigating directed biological, physiological, biochemical and pharmacological processes it is desirable to duplicate physiological cell layers forming boundaries where corresponding processes take place in various parts of the plant, animal or human body, by growing cells of the corresponding type outside their natural environment in the in-vitro system of a tissue culture on a porous or semi-permeable substrate. These cells may be endothelium of the blood or lymphatic vessels, etc., or epithelium of the digestive tract, the bronchia, the kidney, or the like.

The activities taking place at the boundaries may be enzymatic processes, the discharge of substances such as metabolites, hormones, etc., from the cells of the cell layer to the environment, the reception of substances from the environment into the cells, or a movement of substances from the luminal side of the cells through the cells to the basal side thereof, and vice versa.

In order to accurately observe and study the aforesaid activities or processes, the corresponding cells are grown on one side of a substrate mounted in a holding and tensioning device, the substrate being of cellulose acetate or polycarbonate, for example, and having an exemplary pore size of 0.5 microns; the substrate may also comprise a dialysis membrane. The cell layer so established on the substrate is inserted in a perfusion chamber in which a perfusion fluid flows past the cell layer. While the fluid flows past the cell layer, the composition of the perfusion solution will be modified by the biological acitivites in the cells. As a result, the extent of the cell activities may be determined by quantitative comparative analysis of the composition of the inflowing and outflowing perfusion fluids.

In order to be able to study the cell layer in the perfusion chamber while maintaining the integrity of its morphological structure and physiological functions, it is necessary for the substrate to be mounted—already while the cell layer is being established (outside the perfusion system in the tissue culture laboratory)—in a holding and tensioning device and for the latter to be placed in the perfusion system for testing without any mechanical forces acting on the substrate or the cells.

In the aforesaid tests, another problem is that it is difficult to suitably supply the perfusion liquid to the cell chamber (perfusion chamber) and to suitably remove it from the chamber to the test or output side. It has been known to continuously supply the fluid through an inlet to one side of the chamber containing the substrate and to remove it through an outlet on the opposite side of the chamber. In an assembly of this kind the incoming fluid will divide unevenly among the portions of the chamber, depending on chamber symmetry, before being accumulated and discharged. Correspondingly, the cell layer in the chamber will be contacted more or less efficiently in its various portions. In these cases, tests of the perfusion fluid discharged from the chamber cannot yield accurate results because cell processes starting or ceasing suddenly which in some way modify the perfusion fluid surrounding the cells will arrive at the outlet or measuring side of the chamber only after some delay due to the difference in flow path lengths between the chamber inlet and outlet, so that the results will be "blurred"—this undesirable phenomenon is sometimes referred to in laboratory jargon as "tailing".

It is the object of the invention to provide a device for contacting with a perfusion fluid in a perfusion chamber a cell layer grown on a substrate mounted on a holding and tensioning device, the assembly allowing for a sharply eluting perfusion and thus for a precise measurement of the processes taking place at the cells.

This object is achieved by apparatus having the features which will be explained hereinafter.

An advantage of the subject invention is that its careful and sparing treatment of the cells allows for a precise detection of the processes taking place at the cells of their cell layer and their variations in time, so that the physiological phenomena occurring, for example, at the endothelium of the blood or lymphatic vessels, etc., or at the epithelium of the intestinal tract, the bronchia, the kidney, etc., may be duplicated accurately in in vitro tests.

In particular, another advantage of the present invention is that a confluent cell layer grown on a porous or semipermeable substrate may be contacted with the perfusion solution on both sides so that those processes may be detected and duplicated in which the movement of substances takes place through the cell layer from the apical side of the cells to their basal side, and vice versa.

Advantageously, the inventive device is constructed to be disassembled quickly for replacing a substrate mounted in a holding and tensioning device disposed in the perfusion chamber. During re-assembly, the holding and tensioning device mounted in the chamber is preferably received automatically in a manner such that the resultant perfusion chamber will be hermetically sealed on all sides.

Another advantage of the subject invention is that the inventive apparatus operates reliably and safely for extended periods of time and may readily be rendered aseptic by gaseous sterilizing agents.

The invention and embodiments thereof will now be explained in detail with reference to the attached drawings wherein.

Figure 1:
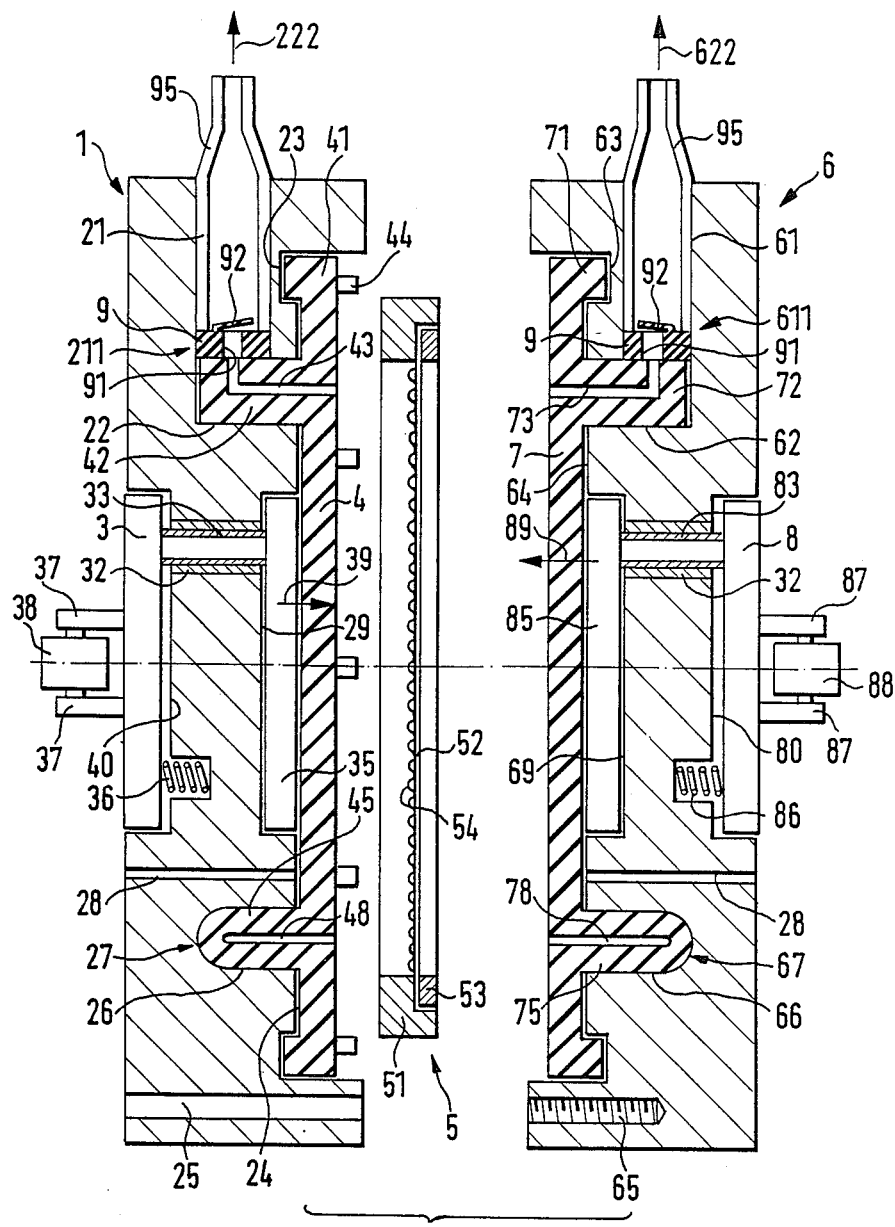
FIG. 1 shows a section through the elements of an inventive apparatus in the disassembled condition thereof.

FIG. 1 shows at 1 in block form a first housing portion of the novel apparatus; reference numeral 6 designates a second housing portion in block form of the inventive apparatus. The two housing portions 1, 6 are adapted to be secured to each other by fastening means not shown in FIG. 1. For example, such fastening means may be threaded bolts extending through openings 25 in housing portion 1 and threaded into the internal threads in tapped blind bores 65 of housing portion 6. Those surfaces of housing portions 1, 6 which face each other in the assembled condition have therein recesses 24 and 64, respectively, each such recess having along its periphery a groove 23 or 63 which extends into the body of housing portion 1, 6 to a greater depth than recesses 24, 64. Laterally of the recesses, the marginal or peripheral areas of housing portions 1, 6 preferably are raised so as to define between the housing portions the aforesaid chamber when the housing is in assembled condition. The housing has external walls and openings extending from the bottom of the first recess 24 and the second recess 64 to the opposite external walls of the housing.

Preferably recesses 24, 64 are circular and grooves 23, 63 are annular in shape.

From the bottom surface of recess 24, a socket or bore 22 extends into housing portion 1 a prescribed distance. That bore ends at an outlet 21 preferably also in the form of a bore of which the longitudinal axis extends perpendicularly, for example, to the longitudinal axis of bore 22 so that bore defining outlet 21 opens to the upper end of housing portion 1 in the manner shown in FIG. 1.

Correspondingly, a socket or bore 62 extends from the bottom surface of recess 64 in housing portion 6 into housing portion 6, said bore 62 communicating with another outlet or bore 61 of which the longitudinal axis preferrably extends at right angles to the longitudinal axis of bore 62.

Correspondingly, another socket or bore 26 extends from the bottom of recess 24 in the housing portion 1 and communicates with an inlet, preferably a bore 27 of which the longitudinal axis perferrably is perpendicular to the longitudinal axis of bore 26 in a manner such that inlet 27 opens to a side surface of housing portion 1.

Also, for forming another inlet, a socket or bore 66 extends into housing portion 6 from the bottom surface of recess 64, said bore 66 communicating with an opening or bore at right angles to the longitudinal axis of bore 66 and forming the additional inlet 67 of the device that opens to one side surface of housing portion 6.

Preferably, housing portions 1, 6 are formed of an autoclavable material such as corrosion-resistant metal. In the manner shown in FIG. 1, a disc-shaped flexible element or elastic wall 4, which preferrably may be an autoclavable silicone rubber element having an annular portion or flange 41 projecting into recess 23, is placed into recess 24. Additionally, element 4 has integral projections 42, 45 engaging bores 22, 26. Projections 42, 45 and element 4 have therein passages 43 and 48, respectively, to connect the exposed surface of element 4 to outlet 21 and to inlet 27, respectively. Analogously, recess 64, bores 62, 66 and groove 63 of housing portion 6 have another disc-shaped flexible element or elastic wall 7 placed therein, said element 7 preferrably being of an autoclavable nature and having an annular portion or flange 71, projections 72, 75 and passages 73, 78. Elements 4, 7 are dimensioned so as to completely fill recesses 24, 64, grooves 23, 63 and bores 22, 62, 26 and 66, respectively, in the assembled condition of the housing.

In particular, projections 42, 72, 45, 75 are dimensioned so that their peripheral portions sealingly engage the corresponding bores 22, 62, 26, 66.

It is of advantage if at least one of elements 4, 7 has provided thereon alignment tabs 44 to receive a holding and tensioning device which mounts a substrate 52 supporting cell layer 54 so that said holding and tensioning device 5, when placed between alignment tabs 44, is concentric with the longitudinal axis of recess 24.

Another recessed area 29 extends from the bottom surface of recess 24 in the housing portion 1 and preferrably is concentric with the recess 24. Recessed area 29 has placed therein a plate 35 preferably of stainless steel. Plate 35 is part of a membrane pump to be explained hereinbelow. Correspondingly, another recessed area 69 extending from the bottom surface of recess 64 in the housing portion 6 and preferably concentric with the recess 64 has placed therein a plate 85 preferably of stainless steel, said plate 85 being part of another membrane pump.

The membrane pumps acts to move plates 35, 85 in the direction of arrows 39, 89, respectively, whereby elements 4, 7 also move in the direction of arrows 39, 89. Outlet 21 and outlet 61 each house a one-way valve 211, 611, respectively, owing to which the perfusion fluid will flow in the direction of arrows 222, 622 only, being prevented from flowing in the opposite directions. In a similar manner, inlets 46, 68 house one-way valves 461 and 681, respectively, which enable a flow of perfusion fluid to take place only from the outside into passage 48 or 78 (FIG. 2).

Figure 2:
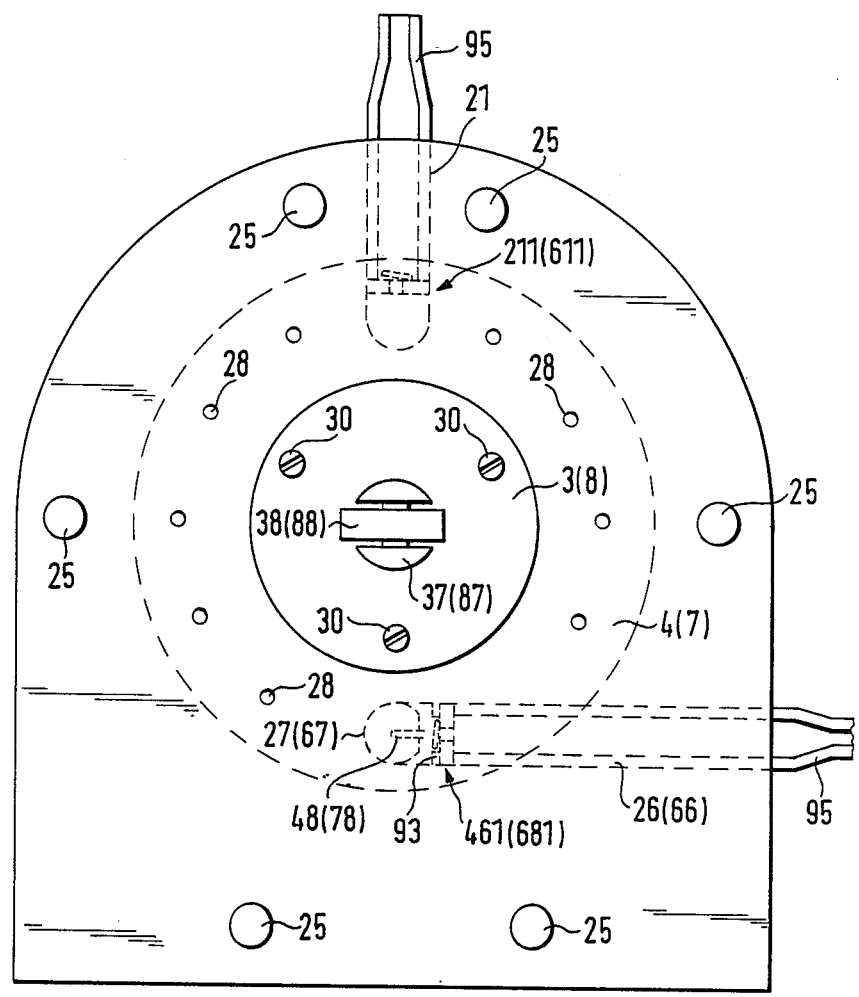
FIG. 2 shows a side view of the inventive apparatus.

In FIG. 2, which shows a side view of housing portion 1, the parenthesized reference numerals designate parts of housing portion 2 which is not itself shown in that side view because it is substantially similar to housing portion 1.

The preferred construction of the valves will now be explained with reference to the valves shown in FIGS. 1 and 2. FIG. 1 shows one-way valves 211, 611 in outlets 21, 61, respectively; FIG. 2 also shows one-way valves 461, 681 in inlets 27, 67, respectively. Preferably, each one-way valve comprises a disc-shaped valve member 9 having an opening 91 therethrough. At one surface of disc-shaped valve member 9 is provided a disc-shaped plate 92 conveniently integral with valve member 9 and adapted to open or close opening 91, depending on the direction of the pressure acting on it. More accurately: Plate or flap member 92 will not close opening 91 in case pressure acts on plate 92 through the opening; in the other case, plate 92 will be urged firmly against the opposite surface of valve member 9, causing opening 91 to be sealed. Preferably, valve member 9 and plate 92 are made of silicone rubber. To provide for the precise and ready engagement of a valve in outlets 21,61 or inlets 27, 67, the openings thereof preferably have therein—as shown in FIG. 2—inwardly projecting shoulders 93 to engage a peripheral area of valve member 9 when the valve is pushed from the outside into an inlet or an outlet. To maintain each valve in position, inserts 95 preferably are threaded into each valve opening so that the lower ends of inserts 95 sealingly engage the valve member 9 and urge them against shoulders 93. In the assembly shown in FIG. 1, the lower ends of inserts 95 urge the valve members 9 directly against the opposite end faces of projections 42, 72. The disc-shaped members of the valves sealingly engage the inner wall surfaces of the respective openings or bores.

In order to prevent the generation of negative pressure behind elements 4, 7 in response to a movement of plates 35, 85 in the direction of arrows 39, 89, FIG. 2 shows passages 28 in housing portions 1, 6 to connect the bottom surfaces of recesses 24, 64 to ambient. As shown in FIG. 2, a plurality of such passages are uniformly spaced about the longitudinal axis of recesses 24, 64. For the sake of simplicity, FIG. 1 shows only one such passage for each housing portion 1, 6.

Spacers 33, 83 in openings in housing portions 1 and 6 respectively couple the plates 35, 85 to plates 3 and 8 disposed in recesses 40, 80 in housing portions 1 and 6, respectively, said recesses 40, 80 being provided in housing portions 1, 6 at the sides opposite recesses 24, 64. Plates 3, 8 are connected rigidly to spacers 33 by fastening means, the latter preferrably comprising threaded bolts 30 (FIG. 2) engaging internal threads in spacers 33. Correspondingly, plates 35, 85 are secured to spacers 33, 83 to establish a rigid connection between plates 3, 35 and 8, 85, respectively. Preferably, friction-reducing sleeves 32 are provided between the outer walls of the spacers 33 and the inner walls of the assocaited openings so as to permit spacers 33 to move in their openings or to facilitate such movement.

Energy storing means—preferrably coil springs 36, 86—are inserted in the recesses extending from the bottom surfaces of recesses 40, 80 into housing portions 1, 6 so as to yieldably bias plates 3, 8 and the elements connected thereto in a defined position in which plates 35, 85 just about engage the opposite sides of elements 4, 7. For example, movement of plates 35, 85 in the direction of arrows 39, 89 is effected by cam followers 38, 88, which are journalled in mounts 37, 87 on outer plates 3, 8, being moved in the direction of arrows 39, 89 by cam members (not shown), with the cam followers preferrably having the form of rollers. As long as said cams do not act on cam followers 38, 88, plates 3, 8 and the elements connected thereto are moved by the force of springs 36, 86 to the aforesaid defined positions in a direction opposite to that shown by arrows 39, 89.

In the inventive apparatus, the length of strokes of plates 39, 89 is limited by the thickness of plates 3, 8 and the depth of recesses 29, 69, the potential stroke length corresponding to the distance between the bottom surfaces of recesses 40, 80 and the opposite sides of plates 3, 8 when the latter assume the aforesaid defined positions. Limiting the lengths of the strokes prevents the cells grown on the substrate from being damaged by the moving members 4, 7.

Figure 3:
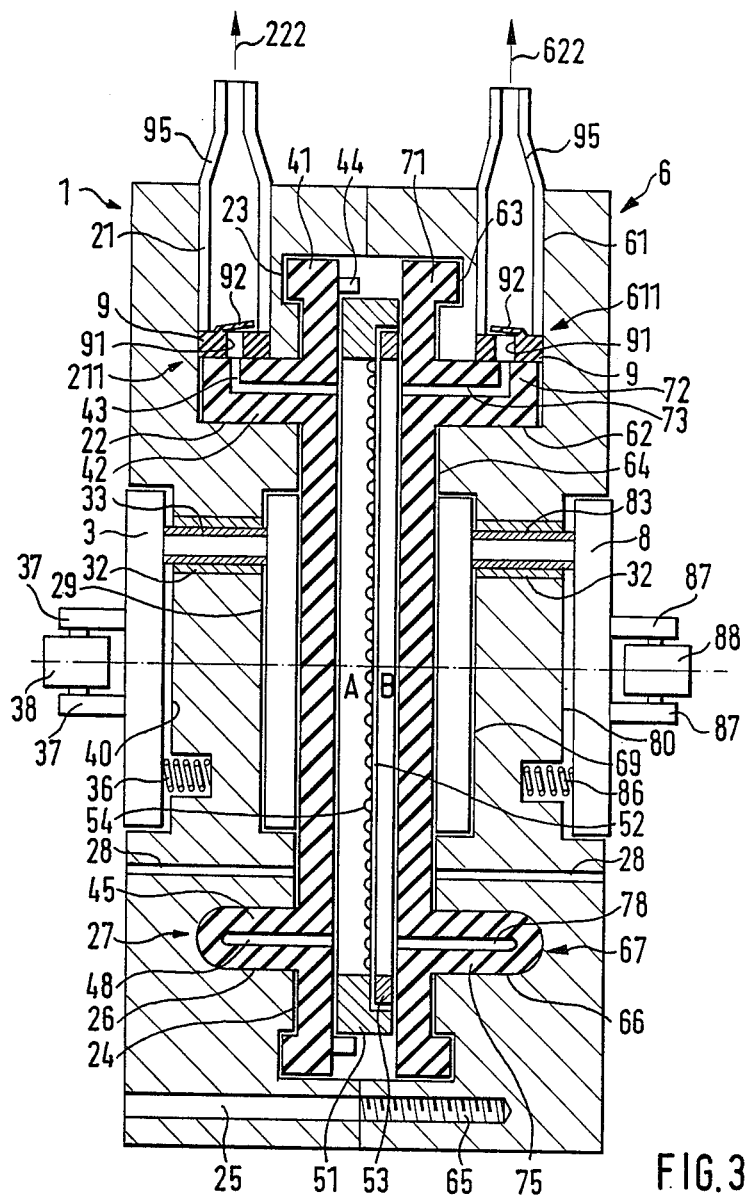
FIG. 3 shows a section through the inventive apparatus in the assembled condition thereof.

FIG. 3 shows portions 1, 6 in the assembled condition to illustrate the operation of the inventive apparatus for contacting with a perfusion solution both sides of a cell layer grown on a substrate. For example, substrate 52 is mounted by a holding and tensioning device 5 removably installed in the housing and comprising two concentric ring members 51, 53 pressed together in the peripheral areas of substrate 52. Reference numeral 54 designates the cell layer grown on one side of substrate 52. During assembly of housing portions 1, 6, holding and tensioning devices 5 is aligned between tabs 44, as mentioned above. When housing portions 1, 6 are secured to each other by fasteners such as screws, those surfaces of concentric ring members 51, 53 which face elements 4, 7, which themselves are of rubber material, are pressed against the elements 4, 7 so that tightly sealed chambers A, B are formed at the sides of substrate 52, the chamber A communicating with outlet 21 through passage 43 and communicating with inlet 46 through passage 48, whereas the chamber B communicates with outlet 61 through passage 73 and communicates with inlet 68 through passage 78. The chambers A and B are defined by the device 5 when the latter is removably installed in the space defined by the assembled portions 1 and 6 of the housing. In chamber A those processes may be detected which take place on the apical side of the cell layer; the processes taking place on the basal side of the cell layer may be detected in chamber B. Inserts 95 in the inlets and outlets and flexible tubes connected thereto (not shown) form the connections to external equipment from which perfusion fluid is supplied under hydrostatic pressure and to which the perfusion fluid is discharged for testing and measurement. In operation of the inventive apparatus, movement of plates 35, 85—and of elements 4, 7—in the direction of arrows 39, 89, as effected by cam followers 38, 88, causes perfusion fluid to flow from chambers A, B through passages 42, 73 and valves 221, 611 to outlets 21, 61. Owing to substantial vortex formation of the fluid in chambers A,B taking place in the process, the perfusion fluid is strongly agitated and mixed so that the changes occurring in the perfusion fluid and the substances dissolved in it due to the cell processes taking place will appear uniformly distributed throughout chambers A, B. In the process, valves 461, 681 (FIG. 2) in inlets 27, 67 will be closed. Movement of plates 35, 85 in a direction opposite to arrows 39, 89 will close valves 221, 611 in outlets 21, 61; also, the valves in inlets 27, 68 will be opened so that perfusion fluid may flow into chambers A, B. At the same time, this movement of plates 35, 85 will cause additional agitation and mixing of the perfusion fluid in chambers A, B.

In order to prevent unidirectional forces from acting upon the cell layer 54 on substrate 52 on the side of substrate 52 opposite layer 54 and from causing damage and disengagement of cell layer 54 from substrate 52, cam followers 38, 88 preferably are controlled so that the plates 35, 85 move in phase, i.e. simultaneously in the direction of arrows 39, 89 or in the direction opposite thereto. In this way, the forces acting from both sides on substrate 52 and on the cell layer 54 grown thereon, which forces have equal magnitudes, will cancel each other so that the only forces remaining to act on the cell layer will be the shear forces generated by the perfusion fluid flow itself; these forces correspond to the physiological blood flow forces, for example.

Figure 4:
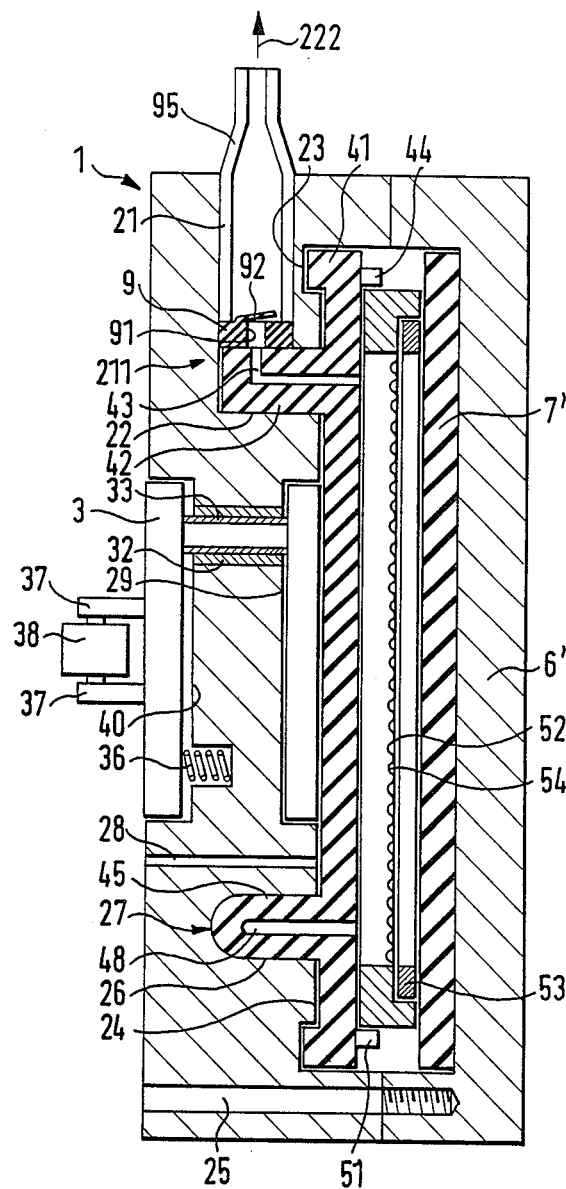
FIG. 4 shows a simplified embodiment of the inventive apparatus.

FIG. 4 shows a simplified embodiment of the inventive papparatus which comprises a single membrane pump. Holding and tensioning device 51, 53, with the substrate 52 mounted therein and the cell layer 54 grown on substrate 54, is placed on element 4, which is contained in the previously described housing portion 1. Instead of housing portion 6, the simplified embodiment includes a housing portion 6' which does not contain a membrane pump. After housing portions 1 and 6' have been secured to each other in the manner previously described, holding and tensioning device 51, 53 sealingly engages at is side facing housing portion 6' a disc-shaped member or element 7' of silicone rubber-like material.

In the modified embodiment, the perfusion fluid is pumped only through the chamber portion between substrate 52 and element 4 of housing portion 1.

The simplified embodiment of the invention is advantageous in case processes and phenomena are to be investigated which take place between the individual cells of cell layer 54 and the perfusion fluid flowing thereover.

I claim:

1. Apparatus for contacting a substrate and a biological single- or multiple-row cell culture thereon with a perfusion fluid, comprising a housing defining a space; a holding and tensioning device arranged to support a substrate with a cell culture thereon and removably installed in said housing so as to divide, with a substrate thereon, said space into a pair of chambers with said device and the substrate therein disposed between said chambers, said housing having a first elastic wall adjacent one of said chambers, a second elastic wall adjacent the other of said chambers, first inlet means for admission of perfusion fluid into said one chamber, first outlet means for evacuation of perfusion fluid from said one chamber, second inlet means for admission of perfusion fluid into said other chamber, and second outlet means for evacuation of perfusion fluid from said other chamber; means for moving said first wall with reference to said device so as to alternatively increase and reduce the volume of said one chamber; first valve means provided in said housing and operative to seal said first inlet means from said one chamber in response to a reduction of the volume of said one chamber and also establish communication between said one chamber and said first inlet means in response to an increase of the volume of said one chamber, respectively; second valve means provided in said housing and operative to establish communication between said one chamber and said first outlet means in response to a reduction of the volume of said one chamber and also seal said one chamber from said first outlet means in response to an increase of the volume of said one chamber, respectively; means for moving said second wall with reference to said device so as to alternatively increase and reduce the volume of said other chamber; third valve means provided in said housing and operative to seal said second inlet means from said other chamber in response to a reduction of the volume of said other chamber and also establish communication between said other chamber and said second inlet means in response to an increase of the volume of said other chamber, respectively; and fourth valve means provided in said housing and operative to establish communication between said other chamber and said second outlet means in response to a reduction of the volume of said other chamber and also seal said second outlet means from said other chamber in response to an increase of the volume of said other chamber, respectively.

2. The apparatus of claim 1, wherein at least one of said walls contains silicone rubber.

3. The apparatus of claim 1, wherein said means for moving said first wall and said means for moving said second wall include means for moving said walls in phase toward and away from each other.

4. The apparatus of claim 1, wherein said housing comprises separable first and second housing portions which jointly define said space, said first inlet and outlet means being provided in one of said housing portions and said second inlet and outlet means being provided in the other of said housing portions, said first and second walls being respectively disposed in said first and said second housing portion, each of said housing portions having a recess for the respective wall and said walls having annular flanges, said recesses including complementary grooves for the flanges of the respective walls and each of said walls further having a first and a second projection extending into a complementary first and second socket in the respective housing portions, said first projections having passages connecting the respective chambers with the corresponding inlet means and said second projections having passages connecting the respective chambers with the corresponding outlet means.

5. The apparatus of claim 1, wherein each of said valve means comprise a one-way valve having a valve member defining an opening for the flow of perfusion fluid and a flap movable with reference to the valve member toward and away from a position in which it seals the respective opening.

6. The apparatus of claim 5, wherein said flaps are integral with the respective valve members.

7. The apparatus of claim 1, wherein said walls have aligning means for maintaining said device in a predetermined position within said space.

8. The apparatus of claim 1, wherein each of said moving means comprises a plate adjacent the respective wall, said housing having recesses for each of said plates and each of said walls being disposed between the respective plate and the corresponding chamber.

9. The apparatus of claim 1, wherein each of said moving means includes means for yieldably biasing the respective wall in a direction to increase the volume of the corresponding chamber.

10. The apparatus of claim 1, wherein said housing has an external surface, a recess for said first wall, and an opening extending from said recess to said external surface, said wall being disposed between said opening and said one chamber.

* * * * *